(12) United States Patent
Danziger

(10) Patent No.: US 9,439,387 B2
(45) Date of Patent: Sep. 13, 2016

(54) LEPIDIUM PLANT NAMED 'DLEPMBEAD'

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 76 days.

(21) Appl. No.: 14/476,508

(22) Filed: Sep. 3, 2014

(65) Prior Publication Data

US 2016/0057964 A1    Mar. 3, 2016

(51) Int. Cl.
*A01H 5/00*    (2006.01)
*A01H 5/12*    (2006.01)
*A01H 1/02*    (2006.01)

(52) U.S. Cl.
CPC ... *A01H 5/12* (2013.01); *A01H 1/02* (2013.01)

(58) Field of Classification Search
None
See application file for complete search history.

(56) References Cited

PUBLICATIONS

Mummenhoff et al 2004, American Journal of Botany 91(2): 254-261.*

* cited by examiner

*Primary Examiner* — David H Kruse
(74) *Attorney, Agent, or Firm* — Cassondra Bright

(57) ABSTRACT

A new and distinct *Lepidium ruderale* plant named 'DLEPEMBEAD' characterized by upright growth habit. Foliage is distinctively pinnatisect, crispate and durable; colored near RHS Green 137B. Plant height commonly averages 90 cm, and foliage produced is an average length of 8 cm long.

5 Claims, 2 Drawing Sheets
(1 of 2 Drawing Sheet(s) Filed in Color)

US 9,439,387 B2

LEPIDIUM PLANT NAMED 'DLEPMBEAD'

FIELD OF THE INVENTION

The present invention relates to a new, distinct and stable variety of *Lepidium ruderale*, hereinafter referred to as 'DLEPEMBEAD'. The present invention relates to seeds which are the *Lepidium ruderale* 'DLEPEMBEAD', as well as, plants and plant parts produced by these seeds which have all of the morphological and physiological characteristics of the *Lepidium ruderale* 'DLEPEMBEAD'. The present invention also relates to methods for producing these seeds and plants of the *Lepidium ruderale* 'DLEPEMBEAD'. Furthermore, the present invention relates to a method of producing progeny *Lepidium* plants by crossing *Lepidium* 'DLEPEMBEAD', as either the female or seed or male or pollen parent, with another *Lepidium* plant and selecting progeny.

BACKGROUND OF THE INVENTION

The present invention relates to a new, distinct and stable variety of *Lepidium ruderale*, and hereinafter referred to by the variety denomination 'DLEPEMBEAD'. The new *Lepidium* 'DLEPEMBEAD' originated from a self-crossing made in a controlled breeding program by the inventor in March 2011, and then first flowered in March 2012, in Mishmar Hashiva, Israel. The parent is the *Lepidium ruderale* proprietary line identified by code LPR-Z-1 (unpatented). This proprietary line is the sole parent, as the resulting 'DLEPEMBEAD' is the result of a self-crossing of this single parent variety.

*Lepidium* is a member of the Brassicaceae family. *Lepidium ruderales* is a vascular land plant, native to temperate Asia and Northern and Eastern Europe. For the most part, plants of *Lepidium rurale* are annual or biennial, producing small or minute flowers.

To the inventor's best knowledge, there have not been significant commercial efforts to date to hybridize and produce new and interesting *Lepidium ruderale* varieties.

Over time, the inventor has trialed *Lepidium* and found it may be advantageously grown for ornamental horticultural uses. Typically, the plants are tolerant of hot, sunny conditions, and require little water.

Leaves of *Lepidium* can be sessile or stalked, normally basally occurring. *Lepidium* plants produce upright spikes of hermaphroditic flowers.

Asexual propagation of *Lepidium* can be performed by vegetative terminal cutings, however, propagation is most commonly performed by sowing seeds.

Methods for cultivation and crossing of *Lepidium* are not well known. Brief reference to the species can be found in: *Brassicaceae, Capparaceae and Cleomaceae of North America Update*, database (version 2011) Updated for ITIS by the Flora of North America Expertise Network, in connection with an update for USDA PLANTS (2007-2010), which is herein incorporated by reference.

The *Lepimedium ruderale* seeds and plants produced by this method are uniform with respect their morphological and physiological characteristics.

A need exists for a greater variety of *Lepidium* cultivars with practical and attractive ornamental features. Additionally, a need exists for additional *Lepidium ruderale* cultivars that can be easily propagated by seed, with consistent results. The new *Lepidium* 'DLEPEMBEAD' was developed through a controlled breeding program and exhibits unique, desirable and stable characteristics.

SUMMARY OF THE INVENTION

The present invention provides *Lepidium* plant selections that produce foliage which is pinnatisect and crispate, on tall plants. This interesting foliage is both novel and useful, as it can be successfully used in flower bouquets as filler plant material. These qualities distinguish the new cultivar from typical *Lepidium ruderale* varieties.

These and other objectives have been achieved in accordance with the present invention which provides 'DLEPEMBEAD' as a new *Lepidium* cultivar that is a product of a planned breeding program conducted by the inventor, Gavriel Danziger, in Moshav Mishmar Hashiva, Israel in 2011. The parent is the *Lepidium ruderale* inbred line identified by code LPR-Z-1 (unpatented).

The parental cultivar has a sufficient degree of homozygosity such that the progeny of the cross are genetypically and phenotypically uniform. The new *ruderale* 'DLEPEMBEAD' therefore can be produced by sexual reproduction by crossing the parent inbred line identified by the code LPR-Z-1 to produce a population of progeny plants, each of which has the combination of characteristics as herein disclosed for the new *Lepidium ruderale* 'DLEPEMBEAD'.

Seeds which are variety 'DLEPEMBEAD' are produced by crossing the parental inbred line identified by the code LPR-Z-1 and are to-be deposited with the Korean Collection for Type Cultures (KCTC), Biological Resource Center, Korea Research Institute of Bioscience and Biotechnology (KRIBB), 125 Gwahak-ro, Yuseong-gu, Daejeon 305-806, Korea having deposit Designation KCTC-12666BP.

OBJECTS OF THE INVENTION

The present invention relates to seeds which produce *Lepidium ruderale* 'DLEPEMBEAD'. The present invention also relates to *Lepidium* plants, and parts thereof; having all the physiological and morphological characteristics of *Lepidium ruderale* 'DLEPEMBEAD'. The present invention relates to a plant produced from seeds which are *Lepidium ruderale* 'DLEPEMBEAD'. The present invention also relates to plant parts, such as pollen, seeds or inflorescence produced by *Lepidium ruderale* 'DLEPEMBEAD'.

The present invention relates to a method of producing seed which are *Lepidium ruderale* 'DLEPEMBEAD', by performing a self-crossing of *Lepidium ruderale* inbred line identified by code LPR-Z-1 (unpatented) and harvesting seeds produced from said cross.

The present invention also relates to a method of producing plants having all the physiological and morphological characteristics of the *Lepidium ruderale* 'DLEPEMBEAD' comprising the steps of (a) self-crossing *Lepidium ruderale* inbred line identified by code LPR-Z-1 (unpatented) (b) harvesting seeds produced from said cross; and (c) producing plants from said harvested seeds.

The present invention also relates to producing progeny plants from the cross of *Lepidium ruderale* 'DLEPEMBEAD', as the female or male parent, with another *Lepidium* plant, and selecting progeny plants from this cross.

BRIEF DESCRIPTION OF THE PHOTOGRAPHS

The patent or application file contains at least one drawing executed in color. Copies of this patent or patent application publication with color drawings will be provided by the Office upon request and payment of the necessary fees.

The accompanying photographs illustrate the overall appearance of the new *Lepidium ruderale* 'DLEPEMBEAD' showing the colors as true as is reasonably possible with colored reproductions of this type. Colors in the photographs may differ slightly from the color values cited in the detailed botanical description which accurately describes the color of 'DLEPEMBEAD'.

DETAILED BOTANICAL DESCRIPTION

Figure 1:
FIG. 1 shows a side view perspective of a typical plant of 'DLEPEMBEAD', at approximately 3 months of age from potting size, grown in a field in Beit Dagan, Israel.
Figure 2:
FIG. 2 shows a close-up view perspective of the foliage.

The present invention was created by the inventor, Gavriel Danziger during 2011, and flowered for the first time in 2012 in Mishmar Hashiva, Israel.

This invention is directed to *Lepidium* plant having all the morphological and physiological characteristics of the variety 'DLEPEMBEAD' produced from seeds which are the product of the self-cross of the *Lepidium ruderale* inbred line identified by code LPR-Z-1 (unpatented). The parent has a sufficient degree of homozygosity such that the progeny of the cross were, and continue to be, phenotypically uniform. The new variety 'DLEPEMBEAD' can therefore be produced by sexual reproduction by crossing of the inbred selection identified by the code LPR-Z-1 to produce a population of progeny plants, each of which has the combination of characteristics herein disclosed for the new variety 'DLEPEMBEAD'.

The following traits have been repeatedly observed and are determined to be unique characteristics of 'DLEPEMBEAD' which in combination distinguish this *Lepidium* as a new and distinct cultivar:

1. Pinnatisect foliage form
2. Crispate foliage
3. Upright growth habit;
4. Durable foliage
5. Mature height around 90 cm
6. Foliage length averaging 8 cm The commercial cultivar known to the present inventor to be the most similar in comparison to the new *Lepidium ruderale* 'DLEPEMBEAD' is the *Lepidium* cultivar 'Ofarim', unpatented. Plants of the new variety 'DLEPEMBEAD' differ from plants of 'DLEPEMBEAD' primarily in foliage type. Foliage of 'DLEPEMBEAD' is pinnatisect whereas foliage of 'Ofarim' is non-dissected. Plants of 'DLEPEMBEAD' flower later compared to plants of 'Ofarim' as well.

'DLEPEMBEAD' has not been tested and observed under all possible environmental conditions. The phenotype of the new cultivar may vary with variations in environment such as temperature, light intensity, frequency of fertilization, composition of fertilizer, acetylene treatment, day length and humidity, without any change in the genotype of the plant.

For example, substantial differences in plant height and diameter, number of leaves, and branches can result depending on the growing conditions. Typically these plants are produced outdoors, and variations in temperature and humidity can produce different results.

The aforementioned photographs, together with the following observations, measurements and values describe the new *Lepidium* 'DLEPEMBEAD' as grown in a greenhouse in Mishmar Hashiva, Israel, under conditions which closely approximate those generally used in commercial practice. Plants of 'DLEPEMBEAD' were grown outdoors with day temperatures ranging from 20° C. to 35° C. and night temperatures ranging from 8° C. to 14° C. Daylength was approximately 12 hours. No artificial lighting or photoperiodic treatments were conducted, but plants of 'DLEPEMBEAD' were treated with growth regulator. Plants were given one treatment of Giberrellic Acid at a concentration of 100 to 200 ppm. Such treatment is common, but not necessary to achieve commercial results Color references are made to the Royal Horticultural Society Colour Chart (RHS), 2005 mini edition, except where general colors of ordinary significance are used. Color values were taken under daylight conditions in a greenhouse Mishmar Hashiva, Israel. The age of the plants of 'DLEPEMBEAD' described is about 90 days from planting a seedling plant. The seedling plant is approximately 5 weeks old.

Botanical Classification:
    *Lepidium ruderale*
Parentage:
    Parent: *Lepidium ruderale* inbred line identified by code LPR-Z-1 (unpatented)
Plant:
Growth Habit: upright
Height: Approximately 90 cm.
Plant Spread: Approximately 50 cm.
Growth Rate: Approximately 4 months to achieve 90 cm.
Branching Characteristics: Moderately well branched.
Length of Primary Lateral Branches: 90 cm.
Diameter of Lateral Branches: 0.7 cm.
Quantity of Primary Lateral Branches: Ranges between to 2-8 per plant
Characteristics of Primary Lateral Branches:
    Diameter: 1 cm.
    Color: Near RHS Yellow-Green 145A
    Texture: Glabrous
    Strength: Strong, firm.
Internode length: Varies along the stem. Approximately 5 cm for the lower part of the stem, and approximately 2 cm for the upper part of the stem.
    Foliage:
Leaf: Most foliage is basal. Cauline leaves occur as well.
The data refers to the basal leaves
    Arrangement: Whorled
    Quantity: Approximately 30 per branch.
    Average Length: 8 cm.
    Average Width: 2.5 cm.
    Shape of blade: Pinnatisect
    Apex: Acute
    Base: Cuneate
    Margin: Entire
    Texture of top surface: Scabrous
    Texture of bottom surface: Scabrous
    Appearance top surface: Matte
    Appearance bottom surface: Matte
    Aspect (flat, wavy, concave, etc): Concave
    Color:
    Young foliage upper side: Near RHS Green 137A
    Young foliage under side: Near RHS Green 137C
    Mature foliage upper side: Near RHS Green 137B
    Mature foliage under side: Near RHS Green 137C
    Venation:
    Type: Arcuate.
    Venation color upper side: Near RHS Green 137D
    Venation color under side: Near RHS Green 137D
    Petiole:
    Length: Average 2 cm.
    Diameter: Average 0.3 cm.
    Color: RHS Near RHS Green 138B
    Texture: Scabrous
    Inflorescence:
Natural flowering season: Spring (February to May in Israel)

Days to flowering from a plantlet: Starting from seeds, approximately 12-16 weeks from planting.
Inflorescence and flower type and habit: The inflorescence type is a spike and the flower type is single, the habit is upright.
Rate of flower opening: 0.5 to 2 days from bud to fully opened flower.
Flower Longevity on Plant: 0.5 to 3 days
Persistent or Self-Cleaning: Self-Cleaning
Bud:
   Shape: Globose
   Length: Average 0.1 cm
   Diameter: Average 0.1 cm
   Color: Near RHS Yellow-Green 145A
Flower size:
   Diameter: Approximately 1 mm.
   Length: Approximately 2 mm.
Corolla/Petals: Not always present.
   Arrangement: Cross shaped
   Length: 0.1 to 0.2 mm
   Width: 0.1-0.5 mm
   Quantity: 4
   Texture: smooth
   Apex: obtuse
   Base: cuneate
   Shape: linear
   Margin: entire
   Aspect: concave
   Color:
   When opening:
   Upper surface: Near RHS White 155A
   Lower surface: Near RHS White 155A
   Fully opened:
   Upper surface: Near RHS White 155C
   Lower surface: Near RHS White 155C
   Aging:
   Upper surface: Near RHS White 155D
   Lower surface: Near RHS White 155D
Calyx/Sepals:
   Quantity per flower: 4
   Shape: oblong
   Length: 0.08-0.7 mm
   Width: 0.04-0.4 mm
   Apex: acute
   Base: cuneate
   Margin: entire
   Texture: smooth
   Color:
   Upper Surface: Near RHS Green 141B
   Lower Surface: Near RHS Green 141B
Peduncle:
   Length: Approximately 0.3-1.3 cm.
   Diameter: Approximately 0.1-0.3 cm.
   Color: Near RHS Yellow-Green 147B
   Orientation: upright
   Texture: smooth
Pedicel:
   Length: Approximately 0.3-0.5 cm.
   Diameter: Approximately 0.03-0.1 cm.
   Color: Near RHS Yellow-Green 146B
   Orientation: upright
   Texture: smooth
Fragrance: Not fragrant
Reproductive Organs:
Stamens:
   Number: 2
   Filament length: Approximately 0.7-0.8 mm.
Anthers:
   Shape: Ovate
   Length: Approximately 0.1-0.2 mm.
   Color: Near RHS Yellow-White 158A
Pistil:
   Style:
   Number: 1
   Length: Approximately 1 mm.
   Color: Near RHS Yellow-Green 147B
   Stigma:
   Shape: two lobed
   Color: Near RHS White 155A
   Ovary Color: Near RHS Yellow-Green 146B
   Temperature tolerance: Tolerates a range from approximately 8° C. to 40° C.
Other Characteristics of Note:
   Color: yellow-green, closest to RHS 1 50D
   Seeds/Fruit:
Fruits
Shape: Elliptic, apically winged.
Length: Approximately 1.8-2.5 mm.
Width: Approximately 1.5-2 mm
Texture: Smooth
Other: Fruiting pedicels are divaricate to horizontal, straight, puberulent
Seeds
Shape: oblong to ovate-oblong
Length: 1-1.5 mm
Width: 0.6-0.8 mm.
   Disease/Pest Resistance and Susceptibility:
Neither resistance nor susceptibility to normal diseases and pests of *Lepidium* observed.

I claim:

1. A *Lepidium* plant named 'DLEPEMBEAD', representative seed deposited at the Korean Collection for Type Cultures (KCTC) having deposit Designation KCTC-12666BP.

2. A *Lepidium* seed that produces the plant of claim 1.

3. A plant part obtained from the *Lepidium* plant of claim 1.

4. A method for producing a *Lepidium* progeny plant comprising the steps of
   (a) crossing *Lepidium* 'DLEPEMBEAD', representative seed having been deposited with the Korean Collection for Type Cultures (KCTC) under Designation KCTC-12666BP as a female or male parent with another *Lepidium* plant, and
   (b) selecting progeny.

5. The method according to claim 4, wherein the second *Lepidium* plant is 'DLEPEMBEAD'.

* * * * *